(12) United States Patent
Zhao et al.

(10) Patent No.: US 9,662,488 B2
(45) Date of Patent: *May 30, 2017

(54) SYSTEMS AND METHODS FOR SELECTIVELY MIGRATING CELLS USING ELECTRIC FIELDS

(71) Applicant: The Regents of the University of California, Oakland, CA (US)

(72) Inventors: Min Zhao, Davis, CA (US); Junfeng Feng, Shanghai (CN); Lei Zhang, Chongqing (CN)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/698,747

(22) Filed: Apr. 28, 2015

(65) Prior Publication Data
US 2015/0246225 A1    Sep. 3, 2015

Related U.S. Application Data

(63) Continuation of application No. 13/831,655, filed on Mar. 15, 2013, now Pat. No. 9,044,611.

(51) Int. Cl.
*A61N 1/18* (2006.01)
*A61N 1/20* (2006.01)
(Continued)

(52) U.S. Cl.
CPC ............ *A61N 1/205* (2013.01); *A61B 5/0476* (2013.01); *A61K 35/30* (2013.01); *A61K 38/18* (2013.01);
(Continued)

(58) Field of Classification Search
CPC .... A61N 1/0464; A61N 1/0468; A61N 1/205; A61N 1/36082; A61N 1/36103; A61K 38/18
(Continued)

(56) References Cited

U.S. PATENT DOCUMENTS 6,366,808 B1    4/2002    Schroeppel et al.
6,708,066 B2    3/2004    Herbst et al.
(Continued)

FOREIGN PATENT DOCUMENTS

EP    2 108 955    10/2009
WO    WO2014/151931 A1    9/2014

OTHER PUBLICATIONS

Arocena, et al., A Time-Lapse and Quantitative Modelling Analysis of Neural Stem Cell Motion in the Absence of Directional Cues and in Electric Fields, Journal of Neuroscience Research, 88:3267-3274 (2010).
(Continued)

*Primary Examiner* — Allen Porter, Jr.
(74) *Attorney, Agent, or Firm* — Foley & Lardner LLP; Antoinette F. Konski; Christopher C. Bolten

(57) ABSTRACT

Systems and methods are provided for migrating cells implanted or endogenous in tissue. The system may include first and second delivery electrodes configured for insertion in tissue and a direct current (DC) power source operatively coupled to the first and second delivery electrodes. The system further may include a programmable controller operatively coupled to the DC power source, wherein the programmable controller is programmed to direct the DC power source to deliver an electric field between the first delivery electrode and the second delivery electrode at a stimulation to nonstimulation ratio sufficient to cause the cells to migrate within tissue selectively.

21 Claims, 12 Drawing Sheets

(51) Int. Cl.
  A61N 1/36    (2006.01)
  A61K 38/18   (2006.01)
  A61B 5/0476  (2006.01)
  A61K 35/30   (2015.01)
(52) U.S. Cl.
  CPC ..... *A61N 1/36082* (2013.01); *A61N 1/36103* (2013.01)
(58) Field of Classification Search
  USPC .............. 607/3, 45, 50; 424/93.7; 435/173.6
  See application file for complete search history.

(56) References Cited

U.S. PATENT DOCUMENTS

| | | | |
|---|---|---|---|
| 6,901,294 B1 | 5/2005 | Whitehurst et al. | |
| 6,944,503 B2 | 9/2005 | Crowe et al. | |
| 7,204,834 B2 | 4/2007 | Schonfeld | |
| 7,412,285 B2 | 8/2008 | Schroeppel et al. | |
| 7,862,551 B2 | 1/2011 | Bates | |
| 2002/0040233 A1 | 4/2002 | George et al. | |
| 2003/0073238 A1* | 4/2003 | Dzekunov | A61K 9/5068 435/461 |
| 2003/0088274 A1 | 5/2003 | Gliner et al. | |
| 2005/0119712 A1 | 6/2005 | Shafer | |
| 2005/0123526 A1 | 6/2005 | Shafer | |
| 2005/0177203 A1 | 8/2005 | Brighton et al. | |
| 2009/0259275 A1 | 10/2009 | Wan | |
| 2010/0152811 A1 | 6/2010 | Flaherty | |
| 2012/0323214 A1 | 12/2012 | Shantha | |
| 2014/0277273 A1 | 9/2014 | Zhao et al. | |

OTHER PUBLICATIONS

Belyy, et al., ecancermedicalscience, Clinical Procedure for intraocular electrochemical lysis during endoresection, eCancer 2013, 7:326 DOI: 10.3332/ecancer.2013.326.
Cao, et al., Endogenous electric currents might guide rostral migration of neuroblasts, European Molecular Biology Organization, Reports, vol. 14, No. 2 (2013).
Chauhan, et al., Evaluating the Biological Effects of Intermittent 1.9 GHz Pulse-Modulated Radiofrequency Fields in a Series of Human-Derived Cell Lines, Radiat Res., 167(1):87-93 (2007).
Chou, et al., Electrochemical Treatment of Localized Tumors with Direct Current, 2nd International Conference on Bioelectromagentism, Feb. 1998, Melbourne Australia, pp. 19-20.
Clark, Encyclopedia of Complementary Health Practice, Part IV—Practices and Treatments, Electrochemical Treatment of Localized Tumors With Direct Current, p. 358 (1999).
Feng, et al., Brief Report: Guided Migration of Neural Stem Cells Derived from Human Embryonic Stem Cells by an Electric Field, Stem Cells, 30:349-355 (2012).
Feng, et al., Tissue-Specific Stem Cells, Brief Report: Guided Migration of Neural Stem Cells Derived from Human Embryonic Stem Cells by an Electric Field, Stem Cells, 30:349-355 (2012).
Hong, et al., Conference Paper-Electrochemical Therapy of Tumors, Conference Papers in Medicine, vol. 2013, Article ID 868319, pp. 1-13 (2013).
International Search Report for Application No. PCT/US2014/026693 dated Jun. 27, 2014.
Kloth, et al., Endogeneous and Exogeneous Electrical Fields for Wound Healing, Biophysical Technologies and Adjunctive Therapies, Part V, Chapter 26, pp. 450-513 (2010).
McCaig, et al., Controlling Cell Behavior Electrically: Current Views and Future Potential, Physiol. Rev. 85:943-978 (2005).
Meng, et al., Electric Field-Controlled Directed Migration of Neural Progenitor Cells in 2D and 3D Environment, Journal of Visualized Experiments, Video Article, http://www.jove.com/details.php?id=3453 (2007).
Meng, et al., PI3K mediated electrotaxis of embryonic and adult neural progenitor cells in the presence of growth factors, Experimental Neurology, doi:10.1016/j.expneurol.2010.11.002 (2010).
O'Clock, The Effects of in Vitro Electrical Stimulation on Eukaryotic Cells: Suppression of Malignant Cell Proliferation, Journal of Orthomolecular Medicine, 12(3):173-181 (1997).
Plotnikov, et al., Effective Treatment of Mouse Metastatic Prostate Cancer by Low Electric Field Enhanced Chemotherapy, The Prostate, 66:1620-1630 (2006).
Pupo, et al., Electrotherapy on Cancer: Experiment and Mathematical Modeling, Current Cancer Treatment—Novel Beyond Conventional Approaches, pp. 585-620 (2011).
Reid, et al., Non-invasive measurement of bioelectric currents with a vibrating probe, Nature Protocols, 2(3):661-669 (2007).
Sannino, et al., Human Fibroblasts and 900 MHz Radiofrequency Radiation: Evaluation of DNA Damage after Exposure and Co-exposure to 3-Chloro-4-(dichloromethyl)-5-Hydroxy-2(5h)-furanone (MX), Radiat Res 171(6):743-51 (2009).
Sauer, et al., Increased doxorubicin uptake and toxicity in multicellular tumour spheroids with DC electrical fields, British Journal of Cancer, 80:1204-1213 (1999).
Sersa, et al., Electrochemotherapy of chest wall breast cancer recurrence, Cancer Treatment Reviews, 38:379-386 (2012).
Song, et al., Application of direct current electric fields to cells and tissues in vitro and modulation of wound electric field in vivo, Nature Protocols, 2(6):1479-1489 (2007).
Tabar, et al., Migration and differentiation of neural precursors derived from human embryonic stem cells in the rat brain, Nat. Biotechnol, 23(5):601-606 (2005).
Takashima, et al., Effects of Continuous and Intermittent Exposure to RF Fields With a Wide Range of SARs on Cell Growth, Survival, and Cell Cycle Distribution, Bioelectromagnetics 27(5):392-400 (2006).
US Notice of Allowance dated Feb. 4, 2015 in U.S. Appl. No. 13/831,655.
US Office Action dated Oct. 23, 2014 in U.S. Appl. No. 13/831,655.
US Office Action dated May 15, 2014 in related U.S. Appl. No. 13/831,655.
Vogl, et al., Prostate Cancer: MR Imaging-guided Galvanotherapy—Technical Development and First Clinical Results, Radiology, 245(3):895-902 (2007).
Wartenberg, et al., Direct Current Electrical Fields Induce Apoptosis in Oral Mucosa Cancer Cells by NADPH Oxidase-Derived Reactive Oxygen Species, Bioelectromagnetics, 29:47-54 (2008).
Wemyss-Holden, et al., The Safety of Electrolytically Induced Hepatic Necrosis in a Pig Model, Aust. N. Z. J. Surg. 70:607-612 (2000).
Wilkinson, et al., Central Nervous System Tissue Engineering, Current Considerations and Strategies, Synthesis Lecture on Tissue Engineering, Chapter 5: Stimulation & Guidance (Entire Book) (2012).
Wu, et al., Directional guidance of neuronal migration in the olfactory system by the protein Slit, Nature, 400(6742):331-336 (1999).
Yao, et al., Electrical Signals Polarize Neuronal Organelles, Direct Neuron Migration, and Orient Cell Division, Hippocampus, 19:855-868 (2009).
Yao, et al., Small Applied Electric Fields Guide Migration of Hippocampal Neurons, Journal of Cellular Physiology, 216:527-535 (2008).
Zhang, et al., Electrically Guiding Migration of Human Induced Pluripotent Stem Cells, Stem Cell Rev and Rep, Published Online, DOI 10.1007/s12015-011-9247-5 (Mar. 5, 2011).
Zhao, Min, Electrical fields in wound healing—An overriding signal that directs cell migration, Seminars in Cell & Developmental Biology, 20:6740682 (2009).

* cited by examiner

SYSTEMS AND METHODS FOR SELECTIVELY MIGRATING CELLS USING ELECTRIC FIELDS

CROSS REFERENCE TO RELATED APPLICATIONS

This application is a continuation under 35 U.S.C. §120 of U.S. patent application Ser. No. 13/831,655, filed Mar. 15, 2013, the entire contents of which are incorporated herein by reference.

STATEMENT OF GOVERNMENT INTEREST

This invention was made with government support under contract number RB1-01417 awarded by the California Institute of Regenerative Medicine. The government has certain rights in the invention.

FIELD OF THE INVENTION

This application generally relates to cell migration within neural tissue, or other types of tissues, using electric fields.

BACKGROUND OF THE INVENTION

Brain damage, brain degenerative disease, and brain disorders generally have a significant impact on functions of the body. Common causes of brain damage include lesions, trauma, and stroke. Difficulty arises in treating such damage, disease, and disorders because neural tissue within the brain cannot regenerate.

Most tissue in the human body originates from undifferentiated cells known as stem cells. These fundamental building blocks differentiate into specific target parenchymal tissue based on hormonal and other local signals. Scientific evidence suggests that stem cells injected into a target tissue will differentiate into a cell line specific to the host tissue. This capability is of particular interest in treating conditions involving organs, such as the spinal cord, heart and brain that cannot regenerate.

Electric fields have been used to guide migration of many types of cells in the laboratory for over a century. Application of electrical stimulation for human and animal health, however, has not been very successful. A major obstacle has been intrinsic detrimental effects associated with direct current electric stimulation, which drastically outweigh the beneficial effects. The electric currents generate heat in the tissue, change pH within the tissue, and produce electrode products that are harmful for cells. Electrical stimulation is further complicated because human tissue is highly conductive, allowing for large current flow which significantly increase the detrimental effects to stimulated tissue. As a result, there are no commercially available devices for direct current brain stimulation at this time to regulate behaviors of neural stem cells and other types of cells in the brain.

In view of the drawbacks of previously known systems, it would be desirable to provide systems and methods for safe and effective direct current brain stimulation.

SUMMARY OF THE INVENTION

The present invention overcomes the drawbacks of previously-known systems by providing systems and methods for migrating cells in tissue, e.g., neural tissue. The system may include first and second delivery electrodes configured for insertion in tissue and a direct current (DC) power source operatively coupled to the first and second delivery electrodes. The system further may include a programmable controller operatively coupled to the DC power source, wherein the programmable controller is programmed to direct the DC power source to deliver an electric field between the first delivery electrode and the second delivery electrode at a stimulation to nonstimulation ratio sufficient to cause the cells (e.g., implanted cells, endogenous cells) to migrate within tissue. Preferably, the stimulation to nonstimulation ratio is in a range from 20 to 1 seconds to 1 to 1 seconds and fractions thereof and the electric field is between 5 mV/mm to 500 mV/mm so as to guide migration without harming the cells (e.g., implanted and/or endogenous stem cells including human neural stem cells (hNSC) and their progenies) and surrounding tissue.

The system may include first and second monitoring electrodes configured for insertion in tissue and configured to monitor the electric field. The programmable controller may be configured to receive a signal indicative of the monitored electric field and to direct the DC power source to deliver an adjusted electric field based on the received signal. The first and second monitoring electrodes may be coupled to a voltmeter configured to measure voltage within tissue and/or coupled to an ammeter configured to measure current within tissue. The system also may include first and second electroencephalogram (EEG) electrodes configured to be inserted in neural tissue or may be disposed on a surface of the scalp. The EEG electrodes are configured to monitor EEG in neural tissue.

In accordance with one aspect of the present invention, the system includes measurement software configured to run on a computer operatively coupled to the programmable controller. The measurement software may be configured to monitor measurements from the programmable controller and to control the programmable controller.

The programmable controller may be configured to deliver the electric field at the stimulation to nonstimulation ratio selected to cause the cells to migrate within tissue while selected natural cells (e.g., astrocytes, neurons, oligodendrocytes, endothelial cells, fibroblast cells, epithelial cells, or any combination thereof) do not migrate or migrate minimally. The programmable controller may be programmed to direct the DC power source to deliver positive charge to the first delivery electrode to generate the electric field or to direct the DC power source to deliver positive charge to the second delivery electrode to generate the electric field or both. In that regard, the programmable controller may be programmed to direct the DC power source to deliver the electric field such that the stem cells migrate toward the first delivery electrode or the second delivery electrode or both. In addition, the programmable controller may be programmed to direct the DC power source to deliver the electric field in a pulsed monophasic or asymmetric biphasic form.

In accordance with yet another aspect of the present invention, a method for migrating cells using an electric field is provided. The method may include inserting first and second delivery electrodes in tissue, e.g., neural tissue, the first and second delivery electrodes operatively coupled to a direct current (DC) power source; and delivering an electric field between the first delivery electrode and the second delivery electrode, via the DC power source, at a stimulation to nonstimulation ratio sufficient to cause the cells to migrate within tissue. The stimulation to nonstimulation ratio may be selected to cause the cells to migrate within tissue while selected natural cells do not migrate or migrate minimally.

The method may include programming a programmable controller with a program having electric field parameters and the stimulation to nonstimulation ratio, wherein delivering the electric field comprises delivering the electric field and the stimulation to nonstimulation ratio according to the program. The method further may include inserting first and second monitoring electrodes in tissue; monitoring the electric field with the first and second monitoring electrodes; receiving a signal indicative of the monitored electric field at the programmable controller; and delivering an adjusted electric field based on the received signal.

In accordance with one aspect, the cells include implanted stem cells and the method further includes implanting the stem cells at an implantation site, e.g., in a rostral migration stream, a subventricular zone, or other parts of a brain. In addition, delivering the electric field may cause the cells to migrate to an olfactory bulb, a subventricular zone, damaged brain tissue due to disease or injury, brain lesions, or any combination thereof.

DETAILED DESCRIPTION OF THE INVENTION

The present invention provides systems and methods for mobilizing and guiding migration of cells for use in regenerative medicine and wound healing. The systems and methods may be used on tissue (e.g., neural tissue) to treat, for example, brain damage (e.g., lesions, trauma, stroke), brain degenerative disease (e.g., Alzheimer's, Parkinson's), and/or brain disorders (e.g., epilepsy, depression). Advantageously, the present invention may be used to stimulate tissue to selectively migrate different cell types (e.g., stem cells including neural stem cells and their progenies, astrocytes, neurons, oligodendrocytes, endothelial cells, fibroblast cells, epithelial cells) by varying a wave form of an electric field (EF) and/or a stimulation to nonstimulation ratio. Unlike nonselective stimulation devices where all or most types of cells in the treated tissue respond to stimulation resulting in unnecessary cell stimulation or even adverse effects on healing and repairing, the present invention selectively guides desired types of cells to desirable sites within tissue for regeneration. The systems and methods described herein are expected to provide safe, power conserving, and effective means for stimulating tissue.

Figure 1:
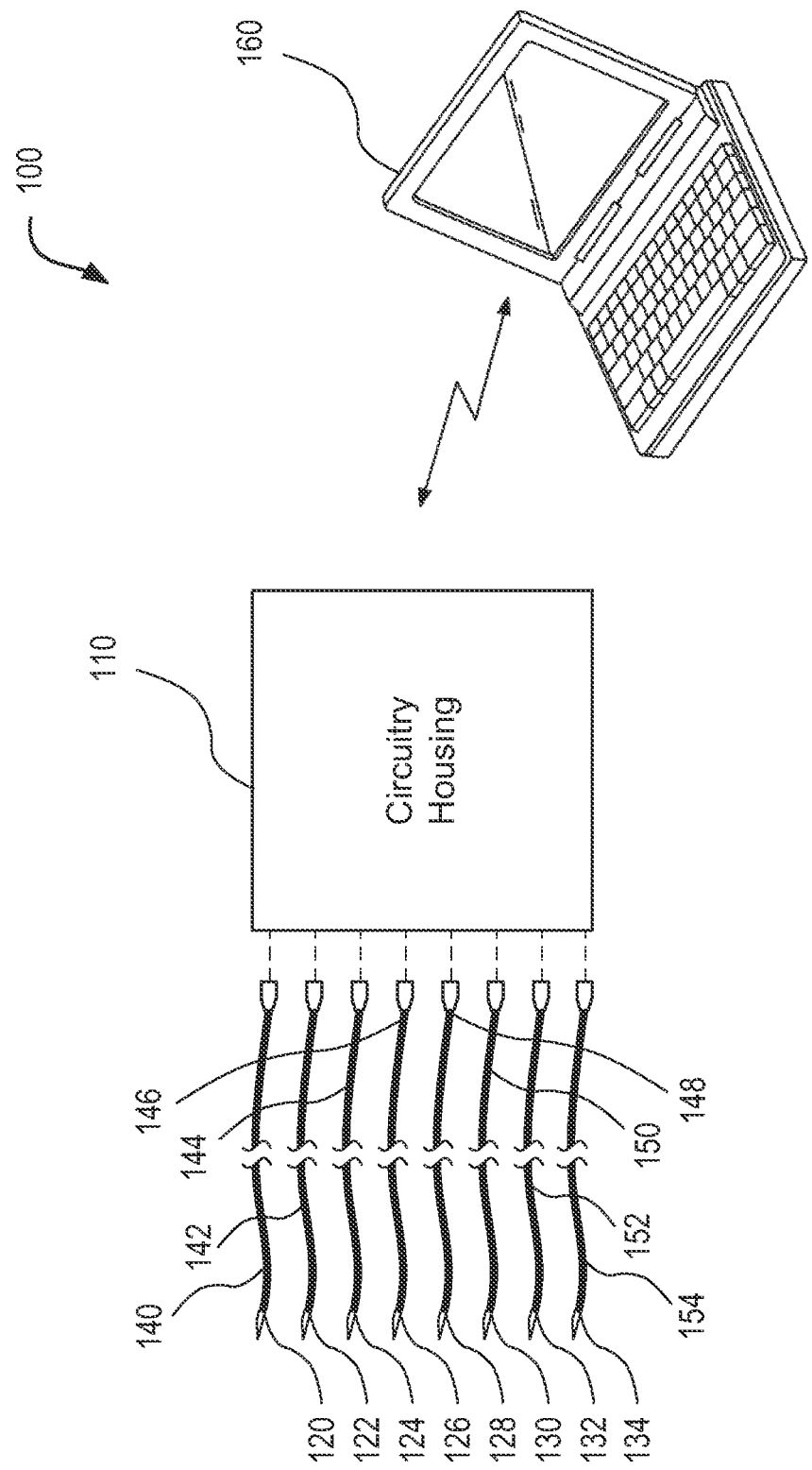
FIG. 1 depicts the components of an exemplary cell migration system constructed in accordance with the principles of the present invention.

Referring now to FIG. 1, an overview of cell migration system 100 of the present invention is provided. In FIG. 1, components of the system are not depicted to scale on either a relative or absolute basis. Cell migration system 100 comprises a plurality of electrodes, circuitry housing 110, and software-based measurement system 160. In the illustrated embodiment, measurement system 160 is installed and run on a conventional laptop computer used by a clinician or hospital. Circuitry housing 110 may be coupled, either wirelessly or using a cable, to measurement system 160 such that measurement system 160 may receive and transmit data to circuitry housing 110.

Circuitry housing 110 is configured to house the control circuitry as well as the power, measurement, communication, and interface components, as described in further detail below. Circuitry housing 110 also preferably includes a data port, such as a USB port, that permits the controller to be coupled to measurement system 160 at a hospital or physician's office. Alternatively, circuitry housing 110 may include a wireless chip, e.g., conforming to the Bluetooth or IEEE 802.11 wireless standards, thereby enabling the controller to communicate wirelessly with measurement system 160. As will be understood by one of ordinary skill in the art, while circuitry housing 110 illustratively includes one housing, multiple housings may be used to house the control circuitry as well as one or more of the other components without departing from the scope of the present invention.

Measurement system 160 is intended primarily for use by the clinician and comprises software configured to run on a conventional laptop or desktop computer that provides a user interface to components within circuitry housing 110. The software enables the clinician to configure, monitor, and control operation of the control circuitry and components within circuitry housing 110 based on programming and/or user input. In a preferred embodiment, measurement system 160 is programmed to allow a clinician to set initial parameters for controlling components within circuitry housing 110 and for starting and stopping measurements, and the components within circuitry housing 110 are configured to automatically run after measurement begins without the need for clinician intervention. In one embodiment, measurement system 160 is configured to shut off the circuitry and/or components and to override a feedback system implemented by the circuitry.

Illustratively, cell migration system 100 includes first and second delivery electrodes 120 and 122, first, second, third, and fourth monitoring electrodes 124, 126, 128, and 130, and first and second electroencephalogram (EEG) electrodes 132 and 134 coupled to circuitry housing 110 via leads 140, 142, 144, 146, 148, 150, 152, and 154, respectively. As will be readily apparent to one of ordinary skill in the art, while FIG. 1 illustrates use of 8 electrodes and 8 leads, the present invention is not limited thereto. For example, one, three, four, or more delivery electrodes, including delivery electrode arrays, may be used; one, two, three, five, six, or more monitoring electrodes may be used; one, three, four, or more EEG electrodes may be used; and a corresponding number of leads may be used.

First and second delivery electrodes 120 and 122 are configured for insertion in tissue, e.g., neural tissue, and may comprise a suitable material for stimulation electrodes such as a metal or carbon. First and second delivery electrodes 120 and 122 are operatively coupled, e.g., via leads 140 and 142, to a direct current (DC) power source, described in detail below. The DC power source is configured to delivery energy to first and second delivery electrodes 120 and 122 to generate an EF therebetween. DC power source may deliver a positive charge to first electrode 120 such that first electrode 120 acts as an anode and second electrode 122 acts as a cathode or may deliver a positive charge to second electrode 122 such that first electrode 120 acts as a cathode and second electrode 122 acts as an anode, or both.

First, second, third, and fourth monitoring electrodes 124, 126, 128, and 130 are configured for insertion in tissue, e.g., neural tissue, and may comprise a suitable material for monitoring electrodes such as a metal (e.g., Ag/AgCl) or carbon. First, second, third, and fourth monitoring electrodes 124, 126, 128, and 130 are operatively coupled, e.g., via leads 144, 146, 148, and 150, to a voltmeter and/or an ammeter, described in detail below. First, second, third, and fourth monitoring electrodes 124, 126, 128, and 130 are configured to monitor the electric field within the tissue including monitoring naturally occurring currents within the brain.

First and second EEG electrodes 132 and 134 may be configured for insertion in neural tissue and may comprise a suitable material for EEG electrodes such as a metal or carbon. First and second EEG electrodes 132 and 134 also may be configured to be disposed on a surface of the scalp using techniques known in the art. As will be readily understood by one of ordinary skill in the art, many EEG electrodes, e.g., over 50, may be disposed on the scalp surface without departing from the scope of the present invention. First and second EEG electrodes 132 and 134 are operatively coupled, e.g., via leads 152 and 154, to an EEG unit, described in detail below. First and second EEG electrodes 132 and 134 are configured to monitor EEG in neural tissue to analyze the effects of the EF.

Figure 2:
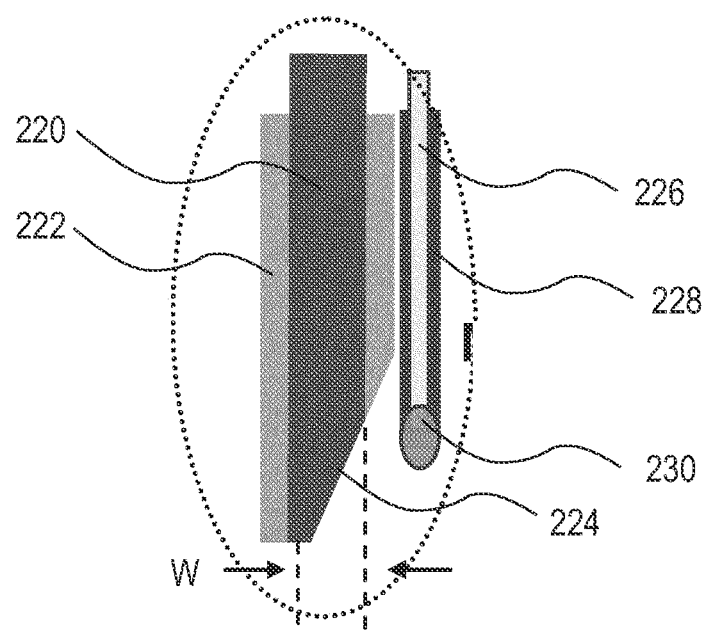
FIG. 2 illustrates the distal region of an exemplary delivery electrode and an exemplary monitoring electrode.

Referring now to FIG. 2, the distal region of an exemplary delivery electrode and monitoring electrode are shown. Delivery electrode 220 is configured similar to delivery electrode 120 described above with respect to FIG. 1. Delivery electrode 220 is encased in insulation 222 except at distal tip 224 where delivery electrode 220 is exposed so as to permit stimulation. Delivery tip 224 optionally may include a beveled or chamfered shape as illustrated. Width W of delivery electrode 220 may be selected as a suitable width for insertion within neural tissue. In a preferred embodiment, width W is 280 μm. Monitoring electrode 226 is configured similar to monitoring electrode 124 described above with respect to FIG. 1. Monitoring electrode 226 is encased in insulation 228 except at distal tip 230 where monitoring electrode 226 is exposed so as to permit electric monitoring.

Figure 3:
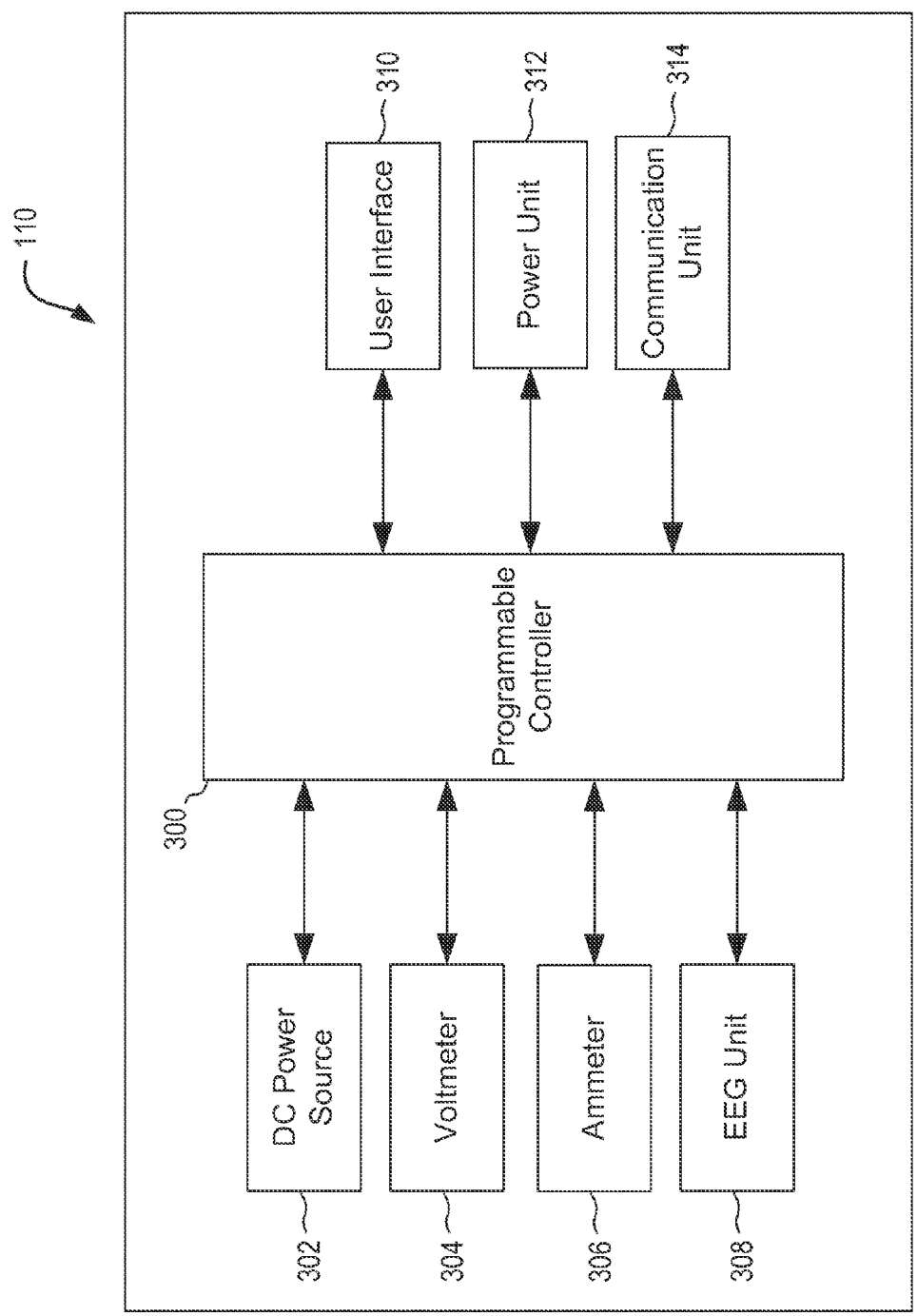
FIG. 3 is a schematic diagram of the circuitry and components disposed within a housing in accordance with an exemplary embodiment of the present invention.

Referring now to FIG. 3, a schematic illustrating the internal circuitry and components of the embodiment of circuitry housing 110 is described. Programmable controller 300 may be electrically coupled to, and configured to control, DC power source 302, voltmeter 304, ammeter 306, EEG unit 308, user interface 310, power unit 312, and/or communication unit 314.

Programmable controller 300 may include one or more microprocessors, controllers, digital signal processors (DSPs), application specific integrated circuits (ASICs), field-programmable gate arrays (FPGAs), or equivalent discrete or integrated digital or analog logic circuitry, and the functions attributed to programmable controller 300 herein may be embodied as software, firmware, hardware, or any combination thereof. Programmable controller 300 may include a volatile memory and nonvolatile memory, e.g., EEPROM, for storing data related to use of system 100, such as user input, treatment settings, measured properties, detected errors, and the like. The memory may store program instructions that, when executed by programmable controller 300, cause programmable controller 300 and system 100 to provide the functionality ascribed to them herein. The memory of programmable controller 300 also may store software downloaded thereon or implemented as a program product and stored on a tangible storage device such as machine-readable medium, e.g., tape, compact disk (CD), digital versatile disk (DVD), blu-ray disk (BD), external nonvolatile memory device, USB, cloud storage, or other tangible storage medium. The software may include computer executable instructions for controlling system 100.

Programmable controller 300 also may store in its memory programs directed to treatment of specific maladies such as brain damage, brain degenerative disease, and/or brain disorders. For example, the program may store electric field parameters and stimulation to nonstimulation ratios that may be selected by a user and/or selected responsive to measured electrical properties within the brain (e.g., current, voltage, electric field, EEG) based on an algorithm or look-up table and/or adjusted responsive to measured electrical properties within the brain based on an algorithm or look-up table. Preselected programs stored in system 100 may be loaded at the manufacturer, or generated using a suitable software program on a conventional personal computer, e.g., measurement system 160, and then uploaded to memory associated with programmable controller 300 via a data port, e.g., USB port, on circuitry housing 110 or communication unit 314, described below. The data port further may be used to retrieve and/or store data on a tangible storage device related to use of system 100, such as user input, treatment settings, measured properties, detected errors, and the like.

Programmable controller 300 preferably also includes preprogrammed safety features, e.g., that shutdown the device if the circuitry or components fail or become disconnected. Programmable controller 300 also may include an error circuit that displays error codes via user interface 310 or measurement system 160.

DC power source 302 is operatively coupled, e.g., via leads 140 and 142, to one or more delivery electrodes, e.g., delivery electrodes 120 and 122 shown in FIG. 1. DC power source 302 may be a suitable DC power source known in the art and is configured to deliver energy to the delivery electrodes such that that an EF is generated between the delivery electrodes. DC power source 302 is operatively coupled to programmable controller 300. Programmable controller 300 may be programmed to direct DC power source 302 to deliver an electric field between the first delivery electrode and the second delivery electrode at a stimulation to nonstimulation ratio sufficient to cause cells (e.g., stem cells, which may be implanted, including human neural stem cells (hNSC) and their progenies) in tissue, e.g., neural tissue, to migrate within the tissue. To minimize injury to tissue, the EF may be between 5 mV/mm to 500 mV/mm, 30 mV/mm to 400 mV/mm, 50 mV/mm to 300 mV/mm, 50 mV/mm to 200 mV/mm, or 30 mV/mm to 100 mV/mm and fractions thereof. For selectively migrating cells and for power conservation, the stimulation to nonstimulation ratio may be in a range from 20 to 1 seconds to 1 to 1 seconds including ratios of 20 to 1, 19 to 1, 18 to 1, 17 to 1, 16 to 1, 15 to 1, 14 to 1, 13 to 1, 12 to 1, 11 to 1, 10 to 1, 9 to 1, 8 to 1, 7 to 1, 6 to 1, 5 to 1, 4 to 1, 3 to 1, 2 to 1, 1.5 to 1, and 1 to 1 and fractions thereof.

In some embodiments, programmable controller 300 is configured to deliver the EF at the stimulation to nonstimulation ratio selected to cause the cells to migrate within tissue while selected natural cells (e.g., astrocytes, neurons, oligodendrocytes, endothelial cells, fibroblast cells, epithelial cells) do not migrate or migrate minimally. Such selective stimulation is expected to cause desired types of cells (e.g., stem cells including hNSC and their progenies) to migrate to desirable sites within tissue (e.g., site of damage or disease) for regeneration while the selected natural cells do not migrate or migrate minimally to prevent adverse effects on healing and repairing. Programmable controller 300 further may be programmed to direct DC power source 302 to deliver the EF in a wave form such as a pulsed monophasic or asymmetric biphasic form. Such selective stimulation also is expected to cause desired types of cells to migrate to desirable sites within tissue while the selected natural cells do not migrate or migrate minimally.

Programmable controller 300 may be programmed to direct DC power source 302 to deliver a positive charge to the first delivery electrode 120 to generate the EF and/or to direct DC power source 302 to deliver a positive charge to the second delivery electrode 122 to generate the EF. In that regard, programmable controller 300 may be programmed to direct DC power source 302 to deliver the EF such that the cells migrate toward the first delivery electrode 120 and/or the second delivery electrode 120. For example, applicants have discovered that applying a positive charge to first delivery electrode 120 causes implanted hNSC to migrate toward second delivery electrode 122 acting as the cathode. Applying a positive charge to second delivery electrode 122 causes implanted hNSC to migrate toward first delivery electrode 120 acting as the cathode. Applicants have further discovered that different types of stem cells react differently to an applied EF. For example, human embryonic stem cells (hESC) migrate toward the delivery electrode acting as the anode when an EF is applied.

In one embodiment, monitoring electrodes, e.g., monitoring electrodes 124, 126, 128, and/or 130 shown in FIG. 1, are configured to monitor the EF generated by the delivery electrodes. In such an embodiment, programmable controller 300 may be configured to receive a signal indicative of the monitored EF from the monitoring electrodes and to direct DC power source 302 to deliver an adjusted EF (e.g., adjusted EF strength, adjusted EF wave form, adjusted stimulation to nonstimulation ratio) based on the received signal. Programmable controller 300 may select the adjusted EF based on the received signal using, for example, user input, an algorithm, and/or a lookup table stored in memory.

Voltmeter 304 is operatively coupled, e.g., via leads 144, 146, 148, and/or 150, to one or more monitoring electrodes, e.g., monitoring electrodes 124, 126, 128, and/or 130 shown in FIG. 1. Voltmeter 304 may include voltmeter components known in the art and is configured to measure voltage based on signals received from the monitoring electrodes. Voltmeter 304 is operatively coupled to programmable controller 300. Programmable controller 300 may be programmed to direct DC power source 302 to deliver the adjusted EF based on the voltage measured by voltmeter 304.

Ammeter 306 is operatively coupled, e.g., via leads 144, 146, 148, and/or 150, to one or more monitoring electrodes, e.g., monitoring electrodes 124, 126, 128, and/or 130 shown in FIG. 1. Ammeter 306 may include ammeter components known in the art and is configured to measure current based on signals received from the monitoring electrodes. Ammeter 306 is operatively coupled to programmable controller 300. Programmable controller 300 may be programmed to direct DC power source 302 to deliver the adjusted EF based on the current measured by ammeter 306.

EEG unit 308 is operatively coupled, e.g., via leads 152 and/or 154, to one or more EEG electrodes, e.g., EEG electrodes 132 and/or 134 shown in FIG. 1. EEG unit 308 may include electroencephalography components known in the art and is configured to measure voltage fluctuations resulting from ionic current flows within the neurons of the brain based on signals received from the EEG electrodes to monitor EEG. EEG unit 308 is operatively coupled to programmable controller 300. Programmable controller 300 may be programmed to direct DC power source 302 to deliver the adjusted EF based on the EEG monitored by EEG unit 308.

The electronics within circuitry housing 110 may be coupled to user interface 310, so that programmable controller 300 actuates system 100 in accordance with input commands or selection of pre-programmed therapy regimes input via user interface 310. User interface 310 may be a display, preferably an OLED or LCD touch screen display, and may include hard buttons, soft button, and/or a plurality of LEDs configured to provide visual confirmation to a user that the components of circuitry housing are powered. The display may display measured properties measured by, for example, monitoring and EEG electrodes such as measured EF, measured voltage, measured current, and measured EEG and may display suitable messages such as error messages.

Power unit 312 may be a port to allow circuitry housing 110 to be plugged into a conventional wall socket, e.g., via a cord with an AC to DC power converter, for powering components within the housing and for charging DC power source 302. Alternatively, power unit 312 may be a suitable battery such as a replaceable battery or rechargeable battery and apparatus may include circuitry for charging the rechargeable battery, and a detachable power cord.

Communication unit 314 is configured to transmit information, such as user input, treatment settings, measured properties (e.g., measured EF, measured voltage, measured current, and measured EEG), detected errors, and the like, to a remote location such as measurement system 160. Communication unit 314 is configured for wired and/or wireless communication over a network such as the Internet or a telephone network using techniques known in the art. Advantageously, communication unit 314 permits a clinician to monitor use of system 100, for example, in embodiments where circuitry housing 110 does not include a display.

In alternative embodiments, one or more of the components supplied within circuitry housing 110 may be omitted.

Methods of using systems for cell migration will now be described with reference to FIGS. 1 through 3.

Figure 4:
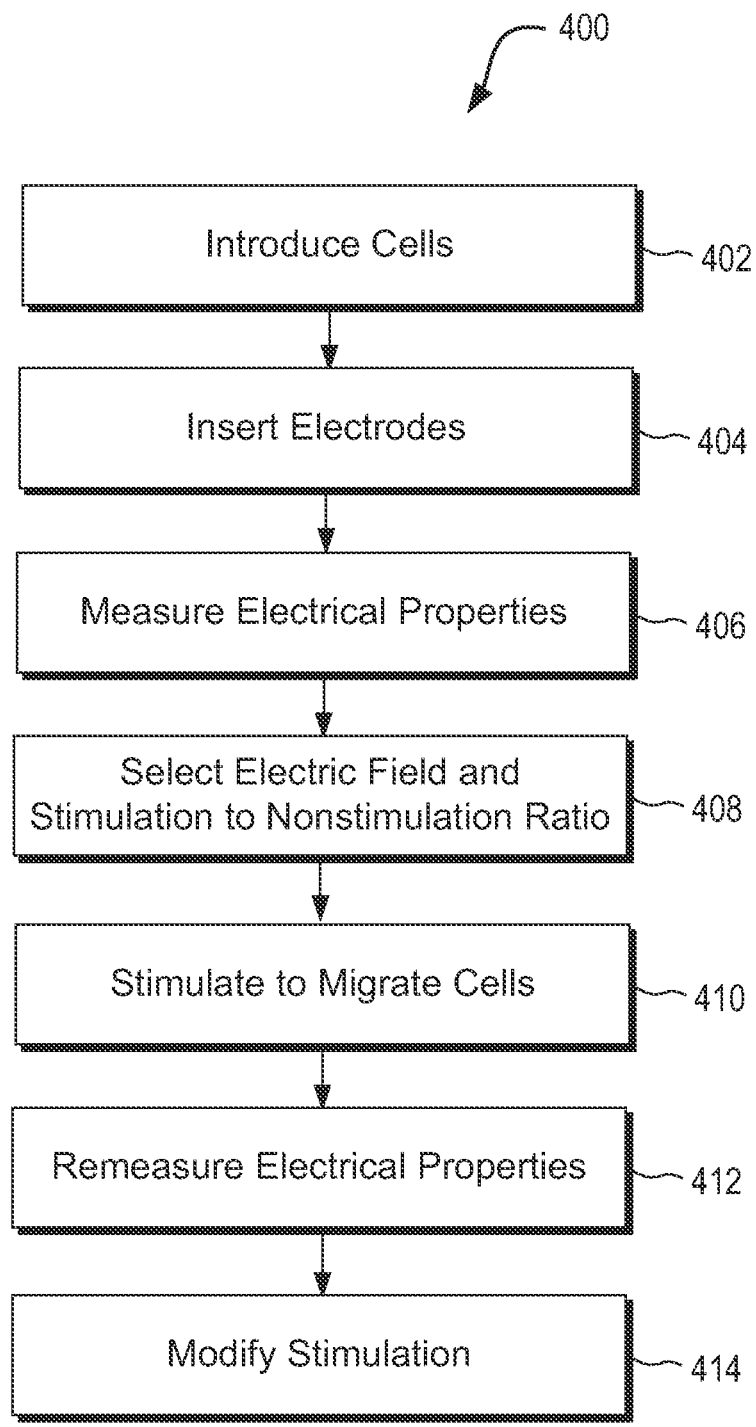
FIG. 4 illustrates an exemplary method for migrating cells using an electric field (EF) in accordance with the principles of the present invention.
Figure 5A:
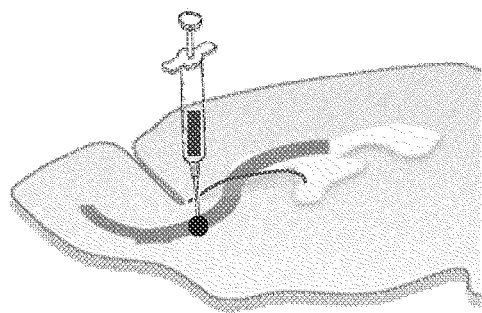
FIG. 5A illustrates an apparatus for implanting cells and FIG. 5B illustrates an exemplary cell migration system constructed in accordance with the principles of the present invention.

FIG. 4 illustrates exemplary method 400 for migrating cells using an EF. At 402, cells (e.g., stem cells including hNSC and their progenies) optionally are introduced. Cells may be implanted in neural tissue using a conventional syringe as shown in FIG. 5A or using an atraumatic delivery apparatus such as described in U.S. Pat. No. 7,862,551 to Bates. Cells may be implanted, for example, in a rostral migration stream, a subventricular zone, and/or other parts of a brain. Alternatively, when the cells are not introduced, the methods of the present invention may be used to migrate cells naturally residing in the body including endogenous stem cells and other repairing cells.

Figure 5B:
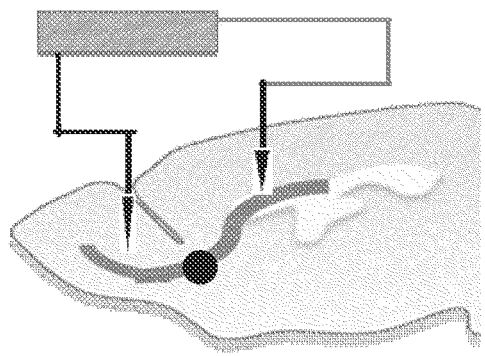

Referring back to FIG. 4, electrodes are inserted within tissue, e.g., neural tissue, at 404. One or more delivery electrodes, e.g., delivery electrodes 120 and 122, may be inserted within neural tissue as shown in FIG. 5B. One or more monitoring electrodes, e.g., monitoring electrodes 124, 126, 128, and/or 130, also may be inserted in neural tissue. One or more EEG electrodes, e.g., EEG electrodes 132 and 134, further may be inserted in neural tissue or may be disposed on a surface of the scalp. Electrodes may be inserted, for example, at the olfactory bulb, the rostral migration stream, the subventricular zone, damaged brain tissue due to disease or injury, and/or brain lesions.

At 406, monitoring electrodes and/or EEG electrodes measure electrical properties such as voltage, current, and EEG within the neural tissue. At 408, programmable controller 300 selects an EF, stimulation to nonstimulation ratio, and/or a wave form using a program based on the measured electrical properties and/or user input at user interface 310 and/or measurement system 160. The stimulation to nonstimulation ratio and/or the wave form may be selected to cause the cells to migrate within tissue while selected natural cells do not migrate or migrate minimally, as described above.

At 410, programmable controller 300 directs DC power source 302 to deliver energy to the delivery electrodes to generate an EF therebetween at the EF strength, stimulation to nonstimulation ratio, and/or wave form according to the program. At 412, the electrical properties such as EF, voltage, current, and EEG are remeasured using the monitoring and/or EEG electrodes and the voltmeter, ammeter, and/or EEG unit. Signals indicative of the remeasured electrical properties are sent to programmable controller 300. At 414, programmable controller 300 determines an adjusted EF based on the signals and/or user input and directs DC power source 302 to deliver the adjusted EF via the delivery electrodes.

Advantageously, the systems and methods described herein are expected to provide safer stimulation because, for example, use of a stimulation to nonstimulation ratio minimizes adverse effects on pH levels within neural tissue. Use of a stimulation to nonstimulation ratio also heats neural tissue less than continuous stimulation to minimize the chances of overheating and damaging neural tissue. The systems and methods further provide beneficial power conserving aspects because use of a stimulation to nonstimulation ratio reduces power consumption of the electronics including DC power source.

As will be apparent to one of ordinary skill in the art, while the systems and methods of the present invention are generally described as guiding cells within neural tissue, it is within the scope of the present invention to migrate cells, e.g., stem cells and their progenies; endothelial cells from small and large blood vessels; fibroblast and smooth muscle cells from vasculature; immune cells including neutrophils, lymphocytes, macrophage; epithelial cells from cornea, skin, kidney, lung, trachea; nerve cells including neurons, neuroblasts, human neural stem cells, mouse neural stem cells, astrocytes; and/or glial cells, anywhere within the body for treatment of trauma, disease, wound healing, and the like. It is also within the scope of the present invention to induce directional tissue growth, e.g. nerve growth and blood vessel formation (angiogenesis).

Examples of the practice of the invention are set forth below. These examples shall not be considered to limit the invention, whose scope is defined by the appended claims.

EXAMPLE 1

Figure 6:
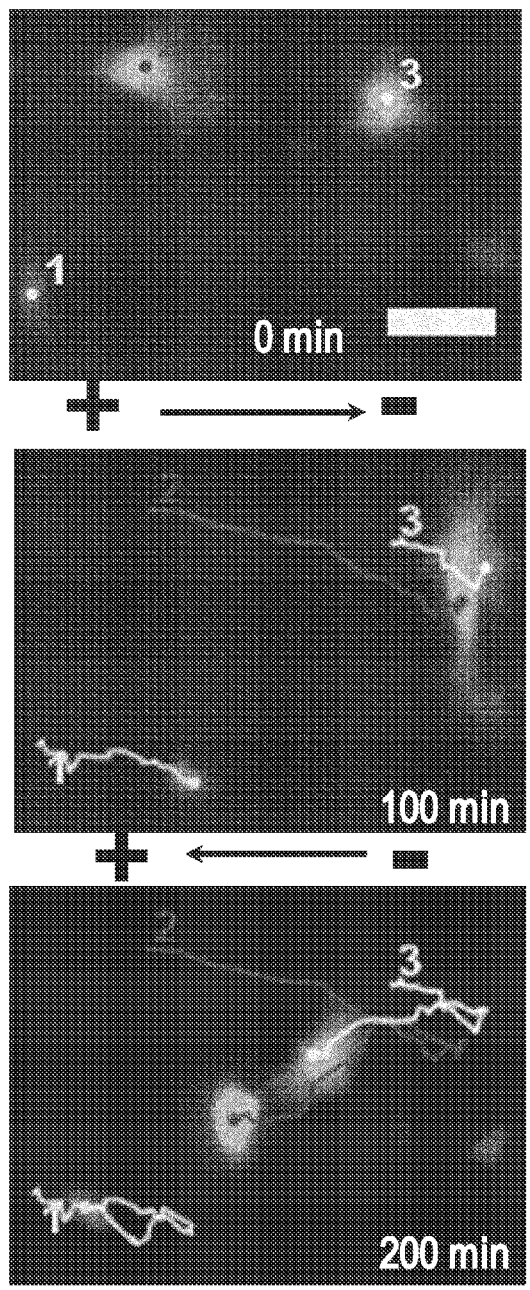
FIG. 6 shows time-lapse images showing directional migration and reversal of migration direction when the field polarity was reversed.

FIG. 6 shows time-lapse images showing directional migration and reversal of migration direction when the field polarity was reversed. The images depict implanted eGFP-hNSCs migrating in response to electric fields. As shown at the 100 minute mark, the eGFP-hNSCs migrated toward the cathode when a positive charge was applied to the left-most delivery electrode to generate an electric field. At the 200 minute mark, the eGFP-hNSCs migrated toward the cathode when a positive charge was applied to the right-most delivery electrode to generate an electric field. FIG. 6 shows that lentivral transfected hNSCs have the same electrotaxis responses as non-transfected cells.

Figure 7:
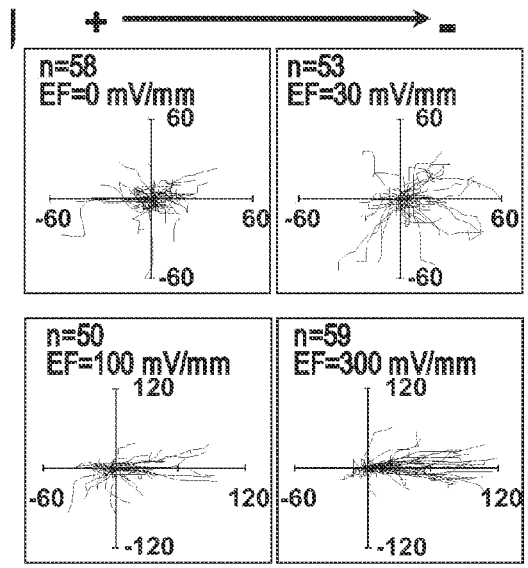
FIGS. 7 and 8 depict migration of cells at various applied EFs strengths.
Figure 8:
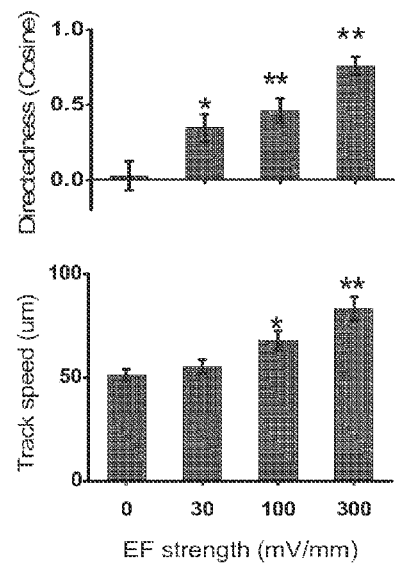

FIGS. 7 and 8 depict migration of cells at applied EFs strengths of 0 mV/mm, 30 mV/mm, 100 mV/mm, and 300 mV/mm. EFs as small as 30 mV/mm induced significant directional migration. An EF of 100 mV/mm or stronger increased migration rate.

EXAMPLE 2

Figure 9:
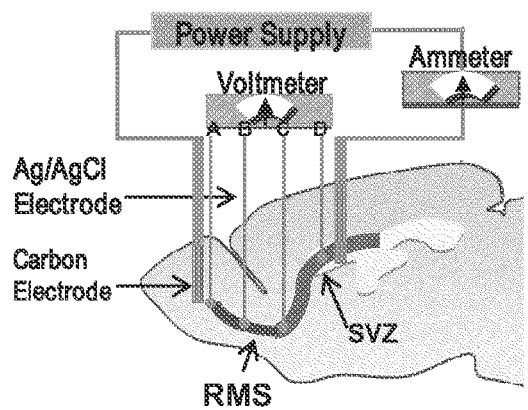
FIG. 9 depicts an experimental setup for delivery and monitoring electric parameters in rat in vivo.
Figure 10:
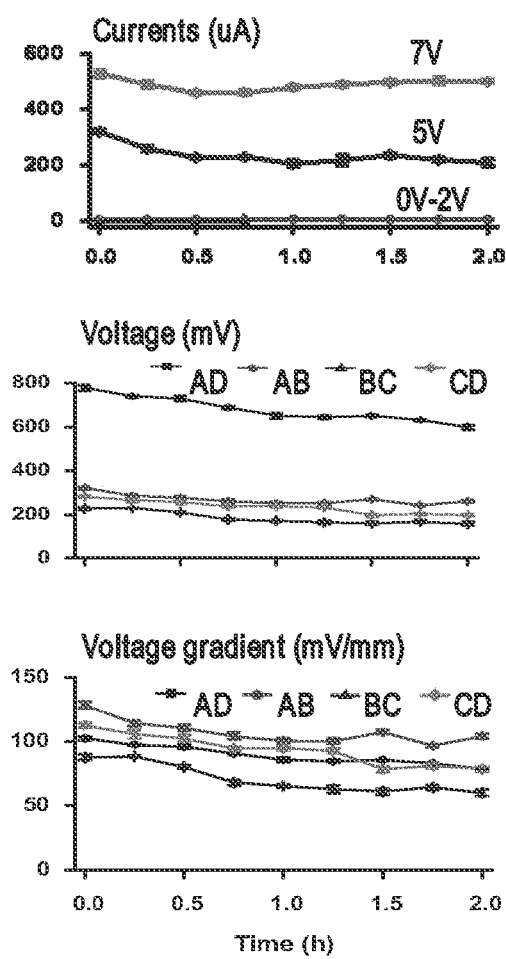
FIG. 10 depicts measured current, voltage, and voltage gradient over time.

FIG. 9 depicts an experimental setup for delivery and monitoring electric parameters in rat in vivo. In the setup, one carbon delivery electrodes was inserted at the olfactory bulb along the rostral migration stream RMS and another carbon delivery electrode was inserted at the subventricular zone SVT along the RMS. Four Ag/AgCl monitoring electrodes were in inserted at four measurement positions (A, B, C and D). FIG. 10 depicts measured current, voltage, and voltage gradient over time. As shown in FIG. 10, when EFs were applied with defined voltage, the currents measured were stable. In addition, the measured voltage and field strength between the four measurement points were shown to be stable.

EXAMPLE 3

Figure 11:
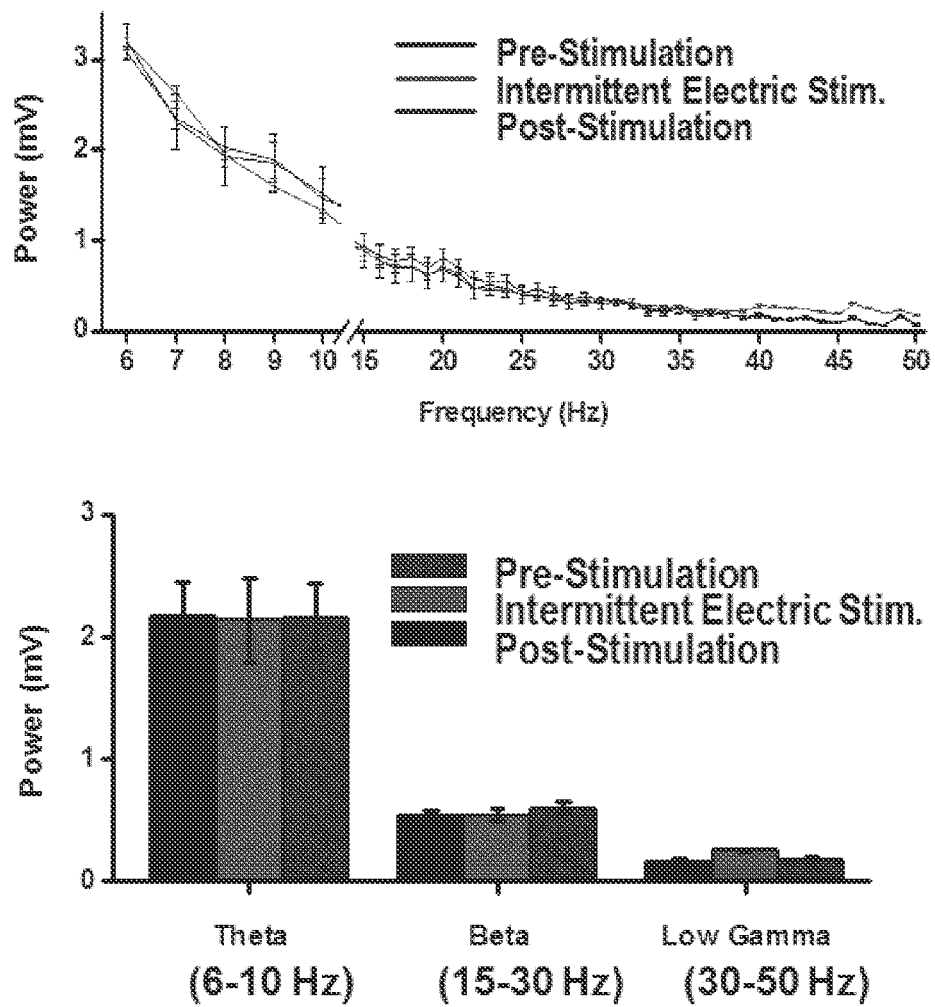
FIG. 11 shows the effects of intermittent electrical stimulation on electroencephalogram as compared to pre-stimulation and post-stimulation EEG.

FIG. 11 shows intermittent electrical stimulation in accordance with the systems and methods of the present invention did not affect EEG (electroencephalogram) at an EF strength of 200 mV/mm as compared to pre-stimulation and post-stimulation EEG.

EXAMPLE 4

Figure 12:
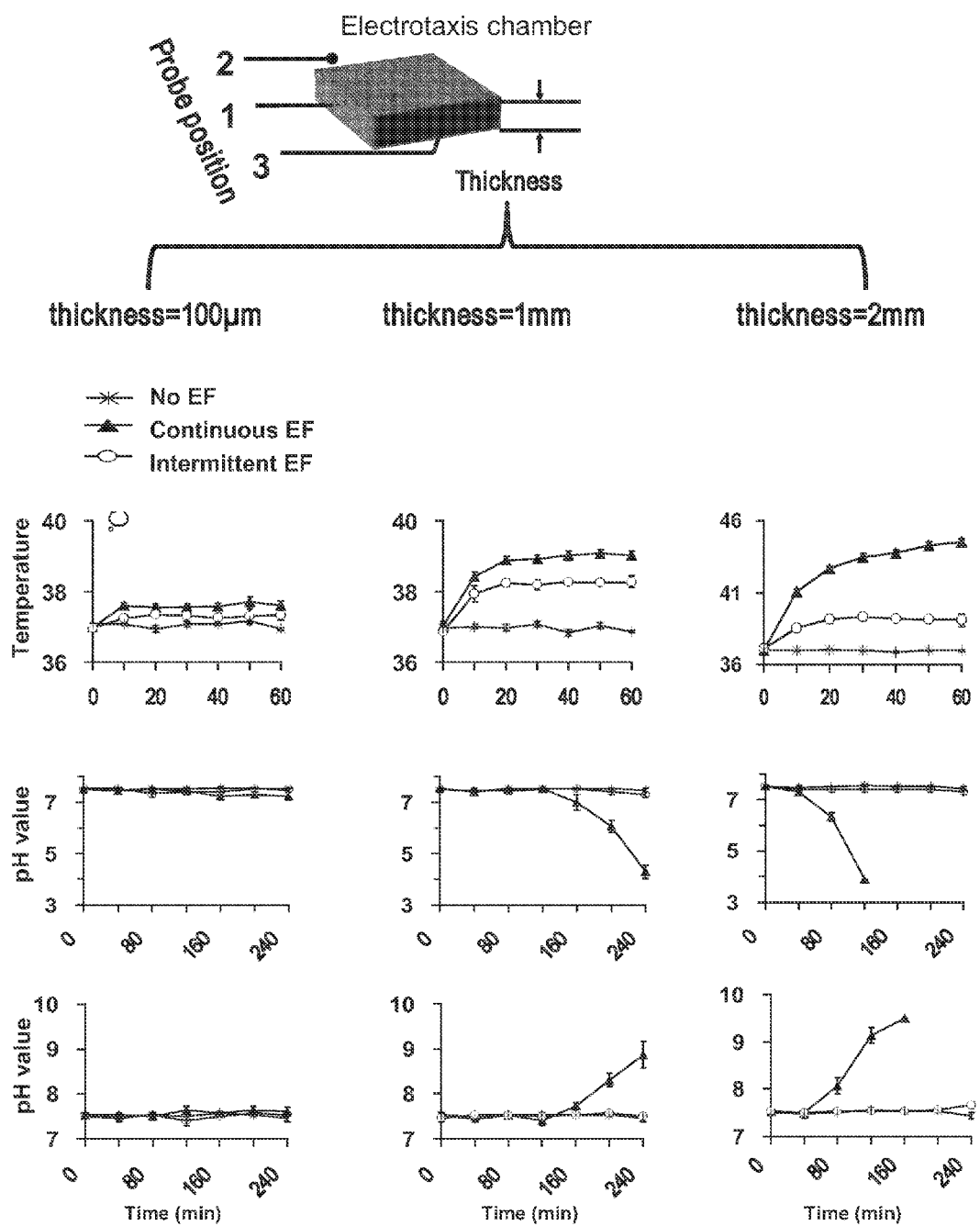
FIG. 12 depicts graphs showing temperature and pH values over time for stimulated tissue having various thicknesses.

FIG. 12 depicts graphs showing temperature and pH values over time for tissue having thicknesses of 100 μm (left-most column), 1 mm (middle column), and 2 mm (right-most column) stimulated at an electric field of 200 mV/mm. The pH value in the middle row was measured at probe position 2 while the pH value in the lower row was measured at probe position 3. As shown in FIG. 12, intermittent stimulation in accordance with the systems and methods of the present invention produced fewer adverse effects regarding temperature and pH value than did continuous stimulation.

EXAMPLE 5

Figure 13:
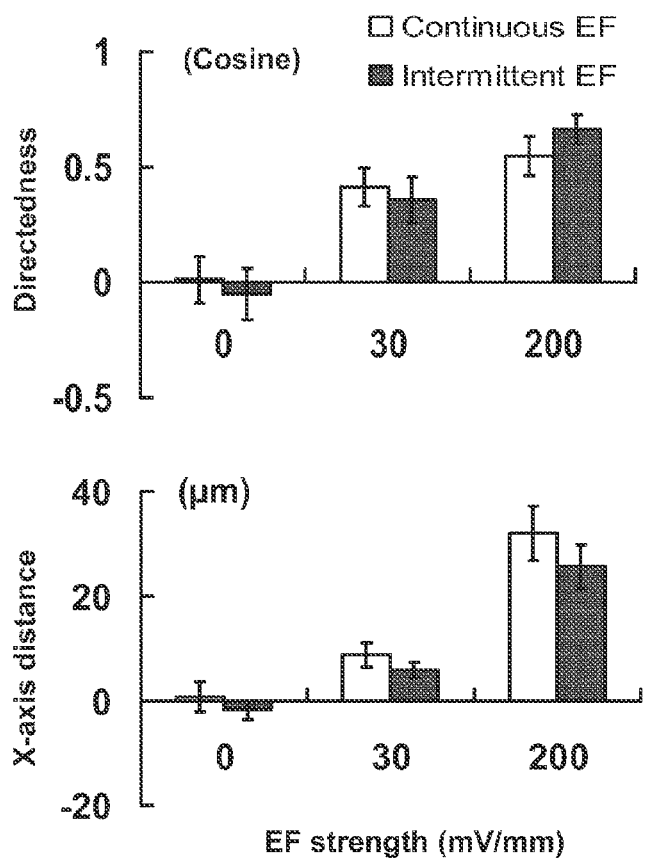
FIG. 13 depicts graphs showing intermittent electrical stimulation achieved significant guidance effect as compared to continuous stimulation.
Figure 14:
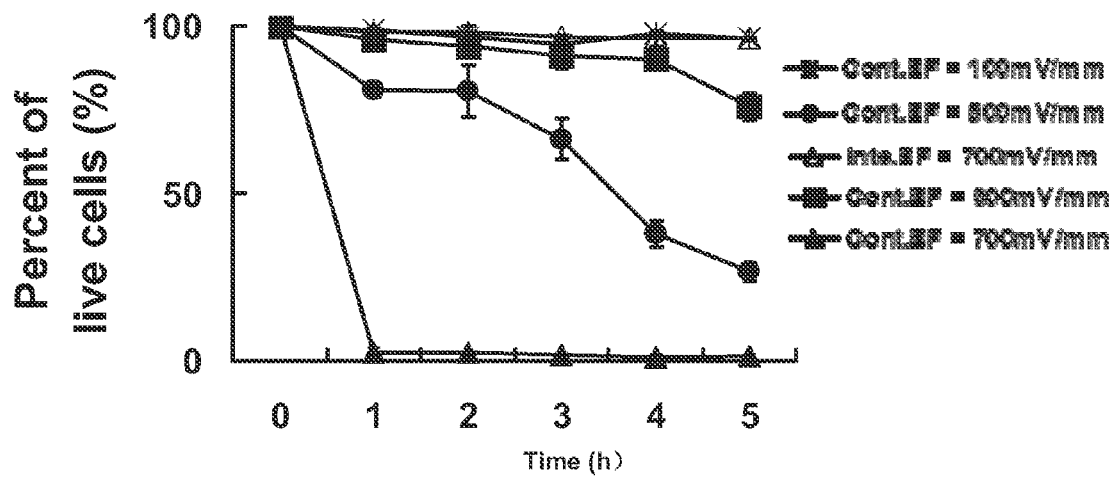
FIG. 14 depicts a graph showing that intermittent electrical stimulation maintains cell viability whereas continuous stimulation can overheat and kill the cells.

FIG. 13 depicts graphs showing that intermittent electrical stimulation in accordance with the systems and methods of the present invention achieved significant guidance effect as compared to continuous stimulation. FIG. 14 depicts a graph showing that intermittent electrical stimulation in accordance with the systems and methods of the present invention maintains cell viability whereas continuous stimulation can overheat and kill the cells.

EXAMPLE 6

Figure 15A:
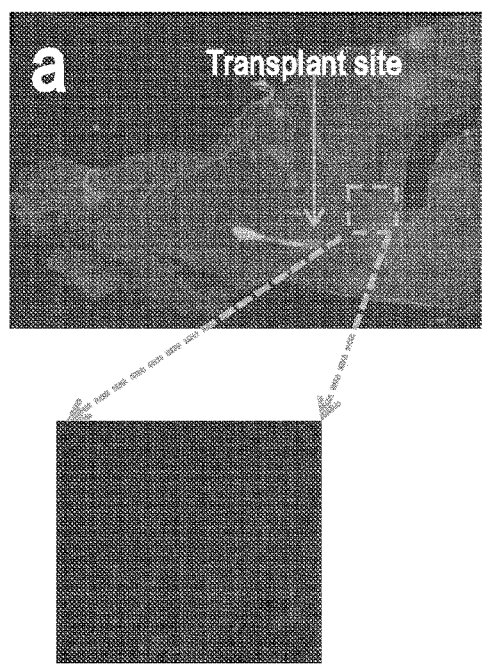
FIG. 15A is an image of a brain in which no EF was applied and FIG. 15B is an image showing that application of electrical stimulation guided migration of human neural stem cells.
Figure 15B:
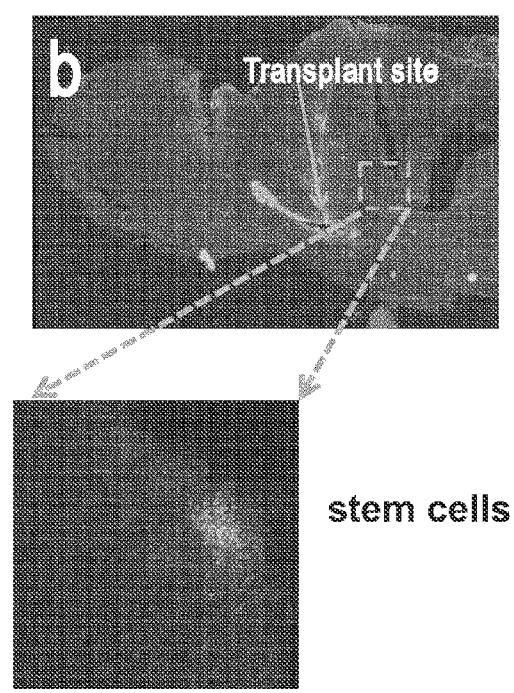

FIG. 15A is an image of a brain in which no EF was applied and showed no migration of transplanted cells while FIG. 15B is an image showing that application of electrical stimulation guided migration of human neural stem cells in rat brain in vivo.

EXAMPLE 7

Figure 16:
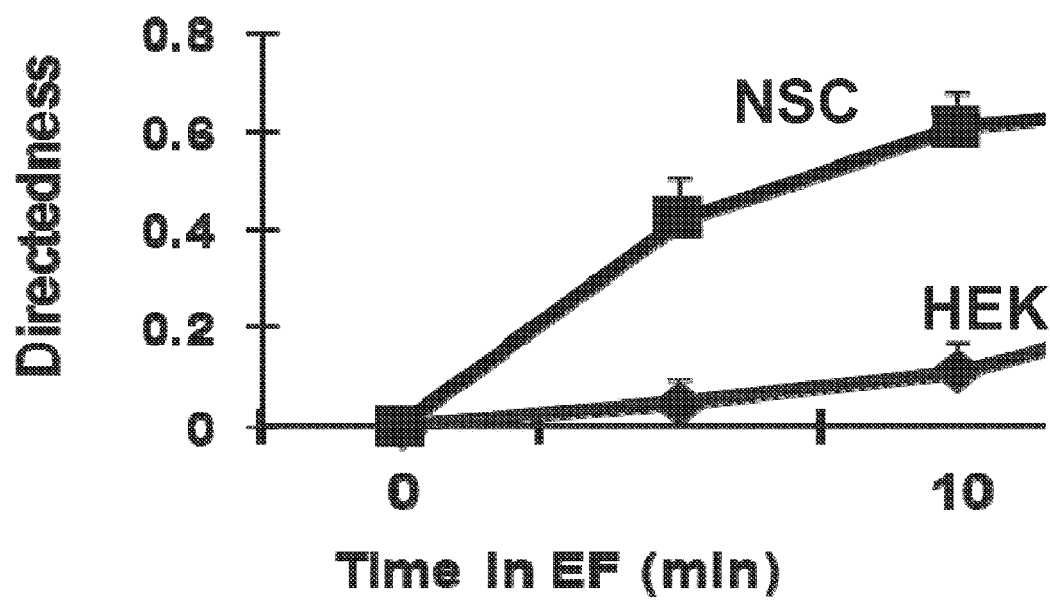
FIG. 16 depicts a graph showing that intermittent electrical stimulation selectively guides migration of human neural stem cells (NSC), but human embryonic kidney cells (HEK) migrate very little as compared to NSC.

FIG. 16 depicts a graph showing that intermittent electrical stimulation in accordance with the systems and methods of the present invention selectively guides migration of human neural stem cells (NSC), but human embryonic kidney cells (HEK) migrate very little as compared to NSC.

Figure 17:
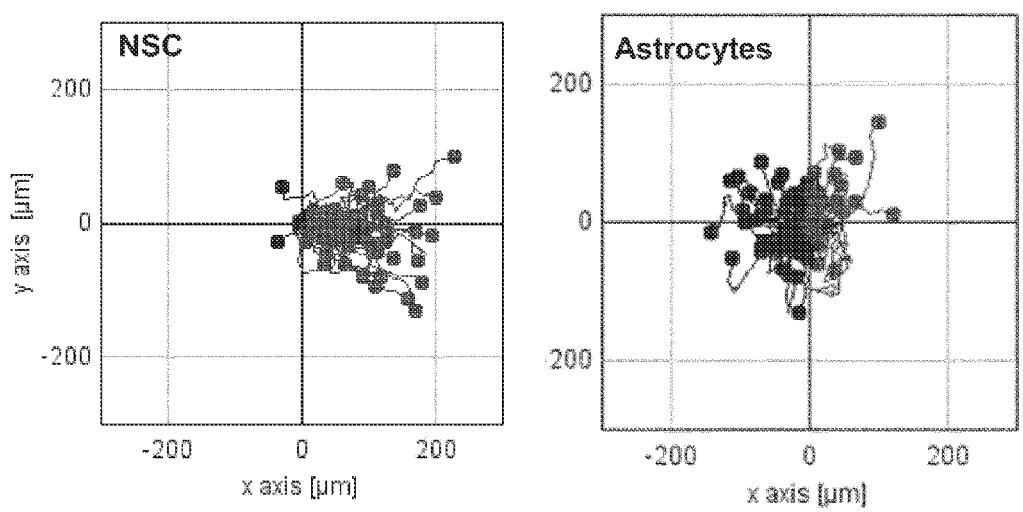
FIG. 17 show that intermittent stimulation selectively guides migration of human NSC, but human astrocytes do not migrate or migrate minimally responsive to such stimulation.

FIG. 17 show that intermittent stimulation in accordance with the systems and methods of the present invention selectively guides migration of human neural stem cells (NSC), but human astrocytes do not migrate or migrate minimally responsive to such stimulation.

While various illustrative embodiments of the invention are described above, it will be apparent to one skilled in the art that various changes and modifications may be made therein without departing from the invention. The appended claims are intended to cover all such changes and modifications that fall within the true scope of the apparatus and methods of the present invention.

What is claimed:

1. A method for migrating cells using an electric field, the method comprising:
    delivering a direct current (DC) electric field into tissue between a first delivery electrode and a second delivery electrode, the first and second delivery electrodes coupled to a circuitry housing via respective delivery leads;
    monitoring strength of the DC electric field within the tissue via first and second monitoring electrodes coupled to the circuitry housing via respective monitoring leads separate from the delivery leads;
    monitoring voltage associated with the DC electric field within the tissue;
    monitoring current associated with the DC electric field within the tissue;
    storing at least one of the monitored electric field strength, voltage, and current; and
    delivering an adjusted DC electric field into the tissue to cause the cells to migrate within the tissue based on at least one of the monitored electric field strength, voltage, or current.

2. The method of claim 1, wherein the tissue comprises neural tissue.

3. The method of claim 1, wherein the cells comprise implanted stem cells and the tissue comprises neural tissue, the method further comprising implanting the stem cells in a rostral migration stream, a subventricular zone, or other parts of a brain.

4. The method of claim 1, wherein delivering the DC electric field causes the cells to migrate to an olfactory bulb, a subventricular zone, damaged brain tissue due to disease or injury, brain lesions, or any combination thereof.

5. The method of claim 1, wherein the cells comprise stem cells and their progenies; endothelial cells from small and large blood vessels; fibroblast and smooth muscle cells from vasculature; immune cells including neutrophils, lymphocytes, macrophage; epithelial cells from cornea, skin, kidney, lung, trachea; nerve cells including neurons, neurablasts, human neural stem cells, mouse neural stem cells, astrocytes; glial cells, or any combination thereof.

6. The method of claim 1, wherein the cells comprise human neural stem cells (hNSC) and their progenies.

7. The method of claim 1, wherein the storing comprises using the circuitry housing operatively coupled to the first delivery electrode and the second delivery electrode to store the monitored electric field strength, voltage, and current.

8. The method of claim 1, further comprising displaying at least one of the monitored electric field strength, voltage, and current using a measurement system running on a computer.

9. The method of claim 1, wherein delivering the adjusted DC electric field comprises delivering the adjusted DC electric field into the tissue at a stimulation to nonstimulation ratio sufficient to cause the cells to migrate within tissue.

10. The method of claim 9, wherein the stimulation to nonstimulation ratio is in a range from 20 to 1 seconds to 1 to 1 seconds and fractions thereof.

11. The method of claim 1, wherein monitoring the voltage comprises monitoring the voltage via a voltmeter within a circuitry housing operatively coupled to the first and second delivery electrodes, and
    wherein monitoring the current comprises monitoring the current via an ammeter within the circuitry housing.

12. The method of claim 1, further comprising generating an electroencephalogram (EEG).

13. The method of claim 1, wherein delivering the adjusted DC electric field comprises delivering the adjusted DC electric field between 5 mV/mm to 500 mV/mm.

14. The method of claim 1, wherein delivering the DC electric field comprises delivering the DC electric field in a pulsed monophasic or asymmetric biphasic form.

15. The method of claim 1, wherein the cells are caused to migrate toward the first delivery electrode or the second delivery electrode or both.

16. The method of claim 1, further comprising inserting the first and second delivery electrodes in neural tissue.

17. The method of claim 1, wherein the first and second delivery electrodes are operatively coupled to a DC power source within the circuitry housing.

18. The method of claim 1, further comprising transmitting information indicative of the monitored electric field strength, voltage, and current using a communication unit.

19. The method of claim 1, further comprising transmitting information indicative of the monitored electric field strength, voltage, and current using a wired connection.

20. The method of claim 1, wherein delivering the adjusted DC electric field comprises delivering the adjusted DC electric field at electric field parameters selected by a user.

21. The method of claim 1, further comprising shutting off delivery of the DC electric field into tissue between the first delivery electrode and the second delivery electrode to override a feedback system.

* * * * *